United States Patent
Lee et al.

(10) Patent No.: US 6,790,840 B1
(45) Date of Patent: Sep. 14, 2004

(54) REVERSIBLY CROSS-LINKED HYDROGELS

(75) Inventors: Kuen Yong Lee, Ann Arbor, MI (US); David J. Mooney, Scio. Township, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 149 days.

(21) Appl. No.: 09/722,010

(22) Filed: Nov. 27, 2000

Related U.S. Application Data

(60) Provisional application No. 60/167,632, filed on Nov. 26, 1999.

(51) Int. Cl.[7] .................. A61K 31/734; A61K 47/36; C08B 37/04; C12N 5/22
(52) U.S. Cl. .................. 514/54; 514/59; 514/60; 536/3; 536/102; 536/105; 536/112; 524/916; 424/92.7; 435/397
(58) Field of Search .................. 514/54, 59, 60; 536/3, 102, 105, 112, 123.12; 524/916; 424/92.7, 423; 435/397

(56) References Cited

U.S. PATENT DOCUMENTS

| | | | |
|---|---|---|---|
| 5,219,564 A | | 6/1993 | Zalipsky et al. |
| 5,874,417 A | * | 2/1999 | Prestwich et al. .......... 514/54 |
| 6,303,585 B1 | * | 10/2001 | Spiro et al. .......... 514/54 |

FOREIGN PATENT DOCUMENTS

| WO | WO 98/1228 | * | 3/1998 |
|---|---|---|---|

OTHER PUBLICATIONS

Bouhadir, K., et al "Synthesis of cross-linked poly(aldehyde guluronate) hydrogels" Polymer, vol 40, pp. 3575–3584, 1999.*

* cited by examiner

Primary Examiner—James O. Wilson
Assistant Examiner—Leigh C. Maier
(74) Attorney, Agent, or Firm—Millen, White, Zelano & Branigan, P.C.

(57) ABSTRACT

A hydrogel composition and methods of preparing and using the same are disclosed. The hydrogel composition comprises an oxidized polysaccharide, and a cross-linker having at least two functional cross-linking groups. The cross-linker reversibly cross-links the polysaccharide and is provided in an amount to provide dangling cross-linkers. The method of preparing a hydrogel comprises the steps of providing an oxidized polysaccharide, and providing a cross-linker having at least two functional cross-linking groups. The cross-linker is mixed with the polysaccharide at a concentration of the cross-linker sufficient to form a hydrogel wherein the cross-linker reversibly cross-links the polysaccharide and has dangling cross-linkers. The hydrogels are useful, for example, for tissue engineering, cell transplantation and drug delivery applications.

14 Claims, 6 Drawing Sheets

REVERSIBLY CROSS-LINKED HYDROGELS

Priority to U.S. Provisional Application Serial No. 60/167,632, filed Nov. 26, 1999 is hereby claimed.

STATEMENT REGARDING FEDERALLY SPONSORED RESEARCH OR DEVELOPMENT

This invention was made in the course of research partially supported by a grant from the National Institute of Health (NIH) (Grant No. R01 DE13033). The U.S. Government has certain rights in the invention.

FIELD OF THE INVENTION

The present invention includes hydrogel compositions and methods for the fabrication and use thereof.

BACKGROUND OF THE INVENTION

Water-containing hydrogels have numerous applications including as food additives, blood contact materials, bioadhesives, contact lenses, wound dressings, artificial organs, drug delivery, controlled release formulations, membranes, superabsorbents, cell encapsulation and immunoisolation materials, and delivery carriers for bioactive agents, including drugs. Their biocompatibility is likely related to their high water content and low interfacial tension with surrounding biological environment. One of the most recent applications of hydrogels is as delivery vehicles of cells for tissue engineering approaches. The aim of this approach is the reconstruction of tissues and organs using three-dimensionally designed synthetic matrices which mimic the function of the extracellular matrix, and offers an alternative to the patient who needs new tissues or organs. Hydrogels may be potent materials for soft tissue engineering applications due to their similarity to the highly hydrated macromolecular-based materials in the body. Critical properties of hydrogels utilized in these applications include their degradation time and mechanical properties. One typically desires to time the rate of hydrogel degradation to the rate of new tissue formation, and this time may vary significantly for different tissues. The mechanical properties of these materials are critical to their ability to create and maintain a space for new tissue formation in vivo, and the mechanical properties of the materials to which cells adhere can also regulate the gene expression of the cells. A number of synthetic and naturally derived materials may be used in the formation of hydrogels. One widely used material in hydrogel formation is alginate, a hydrophilic polysacchoride derived from seaweeds. Alginate comprises a family of natural copolymers of $\beta$-D-mannronic acid and $\alpha$-L-guluronic acid. See Martinsen et al., Biotechnology and Bioengineering, 33: p. 79–89 (1989); Draget et al., Carbohydrate Polymers, 14: p. 159–178 (1991).

One particularly promising application of hydrogels is in tissue engineering. Tissue engineering is directed towards creating biological tissue rather than rely on scarce transplantable organs. An extracellular matrix (ECM) of noncellular material has been identified in many multi-cellular organisms, including human beings. ECM molecules include specialized glycoproteins, proteoglycans, and complex carbohydrates. A wide variety of ECM structures have been identified, and ECM has been implicated in tissue formation. Simply put, the method of tissue engineering is tissue and organ reconstruction using synthetic (e.g., polymeric), three-dimensional matrices, also referred to as "scaffolds" which mimic a body's ECM to provide a space for new tissue formation in vivo. Because alginate exhibits a high degree of biocompatability, is abundant, and inexpensive, it is well suited to application in tissue engineering as well as other applications.

Use of hydrogels in tissue engineering applications particularly is dependent upon hydrogel degradation time and mechanical properties. While alginate is widely employed to fabricate hydrogels for various biomedical applications, ionically cross-linked alginate hydrogels have uncontrollable mechanical properties and disintegration behavior. Preferably, however, hydrogels used in tissue engineering, for example, persist as a tissue generation "scaffold" at least as long as required for new tissue formation. Additionally, the molecular weight of alginate as commonly used in such hydrogels is greater than the limit of renal clearance in humans, such that the disintegrated hydrogel cannot be processed by human kidneys.

Use of hydrogels in injectable form for the delivery of drugs and/or cells has also been of advantageous use. The ability to inject these materials minimizes the pain and cost of delivery to the patient.

Because it is conventionally considered that hydrogel degradation is a function of cross-linking density, one solution to the problem of rapid bydrogel degradation has been the creation of hydrogels characterized by high cross-linking density. However, highly cross-linked hydrogels display mechanical stiffness, an undesirable characteristic particularly in biomedical applications.

What is needed is a hydrogel composition with both desirable mechanical properties and degradation characteristics.

SUMMARY OF THE INVENTION

The hydrogel compositions of the invention are provided with excess reversible cross-linking agent(s) such that some binding sites on the cross-linking agent(s) are initially unbound to the polymer, but are capable of binding to other sites on the polymer as those sites become available through degradation of other cross-links. The cross-linkers which have at least one site bonded to the polymer and at least one site open for reversible bonding will be referred to as dangling cross-linkers or danglers. The conventional view in the art was that such dangling cross-linkers were disadvantageous and to be avoided because the danglers block the site of the polymer to which they are attached. The inventors have discovered, however, how to put this supposed disadvantage to advantageous use according to their invention. For the hydrogels of the invention, the provision of dangling cross-linkers advantageously results in a hydrogel with less mechanical stiffness because not all of the potentially cross-linked sites can be cross-linked due to blocking by the danglers.

It has surprisingly been discovered that the lower mechanical stiffness is not coupled with a corresponding loss of stability to degradation. As cross-linking sites degrade, the presence of the dangling cross-linkers allows formation of new cross-links, thus, compensating for and slowing the degradation rate. The invention therefore results in hydrogels where the mechanical stiffness properties do not have to correspond or be coupled with the degradation properties. In a particular embodiment, hydrogels with desired slow degradation but not with undesired high mechanical stiffness are provided. These hydrogels are particularly useful in drug delivery and tissue engineering applications where it is desirable that the hydrogel not be too stiff to manipulate, administer and/or implant, but which still is resistant to degradation until its function has been served.

The present invention thus relates to an improved polymeric hydrogel composition and method of making the same, and in particular to such a hydrogel composition comprising a hydrogel polymer, preferably an oxidized polysaccharide, and at least one cross-linker having two or more functional groups capable of reversibly cross-linking the polysaccharide in the hydrogel system. The cross-linker is provided as described above to have dangling cross-linkers. In an exemplary hydrogel, the hydrogel polymer is a polysaccharide comprising a synthetic or naturally derived alginate polymer having aldehyde groups, and the cross-linking agent is one having at least two hydrazide groups, such as adipic acid dihydrazide (AAD). Because the hydrogel has preferably many dangling cross-linkers capable of reversibly cross-linking the polymer, the inventive hydrogel compositions display surprisingly improved degradation characteristics and improved mechanical properties as compared with hydrogels having higher cross-linking densities, and/or no dangling cross-linkers.

As indicated, the hydrogel polymer is preferably an oxidized polysaccharide, particularly an alginate. Preferably, such alginate polymer comprises any of several derivatives of alginic acid, including calcium, sodium, or potassium salts or propylene glycol alginate, and most preferably comprises an alginate salt of high guluronate content. The cross-linking agent preferably comprises at least two functional groups which are capable of reversibly cross-linking the polymer, preferably at least two hydrazide groups, and most preferably the cross-linker comprises AAD. Further exemplification of useful polymers and cross-linkers for the hydrogel is provided by reference to WO 98/12228 published Mar. 26, 1998.

The hydrogel polymer and cross-linking agent are admixed in amounts providing an excess of cross-linker so that dangling cross-linkers result and block a high-density extent of cross-linking.

It is preferred that the hydrogels have a cross-linking efficiency for single-end dangling cross-linkers of from 20–90%, more preferably in the range of 20–80%, 20–70% or 30–50%. The creation of significant dangling cross-linkers is facilitated by the use of an excess amount of cross-linker. Also, it is preferred that hydrogel formation be conducted in a salt solution. Such solution preferably contains 0.01–20 g/l (more preferably 2.0–10.0 g/l) of NaCl and may optionally additionally contain one or more of:

| | |
|---|---|
| 0.01–1.0 | (pref. 0.1–0.5) g/L of $CaCl_2$; |
| 0.01–2.0 | (pref. 0.2–1.0) g/L of KCl; |
| 0.01–1.0 | (pref. 0.05–0.5) g/L of $NaH_2PO_4 \cdot H_2O$; or |
| 0.01–1.0 | (pref. 0.05–0.5) g/L of $MgSO_4$. |

The hydrogel polymer is preferably of low molecular weight (Mw) so as to be suited for biomedical applications. However, applications using hydrogels with molecular weight up to 50,000 Daltons are possible. Hydrogels with molecular weight (Mw) from 1,000 to 30,000 or 1,000 to 10,000 are more preferred. Molecular weight can be modified by means such as acid hydrolysis and oxidation, as necessary. According to the illustrated example, an alginate material is hydrolyzed under acidic conditions to yield sodium poly(guluronate) (PG) of relatively low molecular weight (e.g. Mw about 7,000). The PG precipitate is then oxidized by sodium periodate to form the alginate polymer, PAG (e.g. Mw about 5,700). This PAG intermediate is subsequently cross-linked with a suitable cross-linker, such as AAD, in the manner discussed above to form hydrogels with dangling cross-linkers.

The resultant PAG hydrogels exhibited a higher degree of swelling (Q) and lower shear modulus (G) than PAG hydrogels with a higher cross-linking density (e.g., those on the order of $16.0 \times 10^5$ mol/$cm^3$ or higher). The preferred degree of swelling (Q) is from 1 to 200, more preferably 5 to 100. The preferred shear modulus (G) is from 0.005 to 200 kPa, more preferably 0.05 to 100 kPa.

The hydrogels are further characterized by increased stability over time; that is, slower degradation. Hydrogels having this characteristic retarded degradation imparted by reversibly cross-linking dangling cross-linkers are well suited to numerous applications, including biomedical applications such as tissue engineering cell transplantation and drug delivery. Further discussion of useful applications is provided by reference to WO 98/12228 published Mar. 26, 1998.

The present invention relates to polymer hydrogel compositions and methods of making and using the same, and particularly to hydrogels characterized by a cross-linker having at least two functional groups able to reversibly cross-link the polymer. The hydrogels are further characterized by an extent of cross-linking such that some potentially cross-linkable sites are not cross-linked because two dangling cross-linkers are occupying sites which are cross-linkable by a single cross-linker. Such hydrogels display improved mechanical properties and retarded degradation as compared to conventional hydrogel systems.

As used herein, the term "hydrogel" refers to a three-dimensional network of cross-linked hydrophilic polymers comprising water. Hydrogels are preferably, though not necessarily, limited to gels. Hydrogels may have a net positive or negative charge, or may be neutral.

The term "cross-linking" and formatives thereof, as used herein refers to an attachment of two chains of polymer molecules by bridges, composed of either an element, a group, or a compound, that join certain atoms of the chains by chemical bonds. Cross-linking can be effected naturally and artificially. Internal cross-linking between two sites on a single polymer molecular is also possible.

The terms "cross-linker: or "cross-linking agent", as used herein, refers to the element, group, or compound that effects cross-linking between polymer chains.

The term "dangling cross-linkers" or "dangler" refers to cross-linkers having at least one site bonded to the hydrogel polymer and at least one site remaining free and capable of subsequent bonding to the polymer.

The term "reversibly cross-linking", and formatives thereof, as used herein refers to the phenomenon of degradation and reformation of cross-links over time in a degradable hydrogel system.

Figure 1:
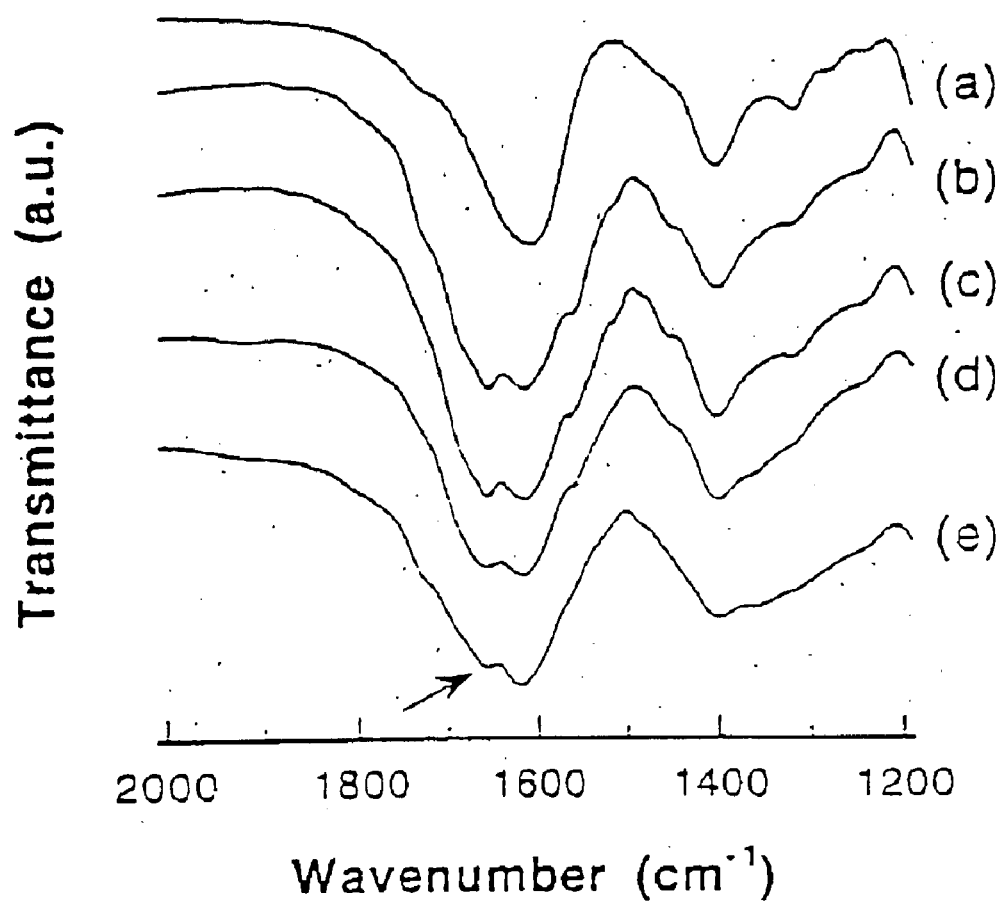
FIG. 1 is a plot of the characteristic infrared absorption bands for PAG and for a PAG hydrogel cross-linked with 150 mM AAD over time.

The entire disclosure of the priority application U.S. Provisional Application Serial No. 60/167,632, filed Nov. 26, 1999, of K. Y. Lee et al., *Macromolecules*, published January 2000, and of all other patents, applications and publications referred to above or below are hereby incorporated by reference.

EXAMPLES

In the foregoing and in the following examples, all temperatures are set forth uncorrected in degrees Celsius; and, unless otherwise indicated, all parts and percentages are by weight.

Hydrogel Preparation

In brief, the exemplary hydrogel of the present invention is prepared by cross-linking a hydrogel polymer, preferably an oxidized polysacharide such as an alginate polymer, with a cross-linking agent having at least two functional groups, the cross-linking agent capable of reversibly cross-linking the polymer and provided in an amount to result in the discussed dangling cross-linkers. In the exemplary embodiment, the hydrogel polymer is an alginate cross-linked with a cross-linker having two hydrazide functional groups, the polymer and cross-linker admixed in relative amounts such that the resultant hydrogel is characterized by the presence of a significant amount of dangling cross-linkers. The hydrogel preferably has a relatively low cross-linking density, as determined by the Flory-Rehner equation. In an exemplary hydrogel system comprising poly(aldehyde guluronate) (PAG) cross-linked with AAD, the preferred cross-linking density (Ve) is less than $16.0 \times 10^5$ mol/cm$^3$, and most preferably less than approximately $12.3 \times 10^5$ mol/cm$^3$.

According to the illustrated examples, polymer bydrogels were generally prepared by hydrolyzing an alginate under acidic conditions, isolating and subsequently oxidizing polyguluronate (PG) therefrom to prepare poly(aldehyde guluronate) (PAG), and cross-linking the PAG (20% wt solution) with a cross-linker having at least two hydrazide groups, for example adipic acid dihydrazide (AAD), to form hydrogels. The concentration of cross-linker was varied from 50 mM to 250 mM.

The hydrogel polymer preferably comprises an oxidized polysaccharide, for example an alginate such as the commercially available sodium alginate (PROTANAL LF 20/60) obtained from PRONOVA (Drammen, Normay). Preferably, such alginate is characterized by a high guluronate content, since the guluronate units provide sites for ionic cross-linking through divalent cations to gel the polymer. However, it will be understood that a variety of alginates may serve for the present invention. "Alginate", as that term is used herein, refers to any of a number of derivatives of alginic acid (e.g., calcium, sodium, or potassium salts or propylene glycol alginate). These compounds may be synthetic or naturally derived. Both natural and synthetic alginates are commercially available or may be prepared, and may be substituted in preparation of the present inventive hydrogel according to this disclosure. Natural source alginates may be derived from seaweed or bacteria according to conventional methods. See *Biomaterials: Novel Materials from Biolopical Sources*, ed. Byrum, *Alginates* chapter (ed. Sutherland), p. 309–331 (1991). Both naturally derived and synthetically prepared alginates can be fabricated, according to known methods, to provide side chains with a desired mannuronate and guluronate proportion. It is not intended that the present invention be limited to alginate or any particular polymer, or a particular method of making the same. For instance, any of a number of polysaccharides, both synthetic and naturally derived, including cellulose, agarose, dextran, pullulan, starch, hyaluronate, etc., may be substituted for the alginate of the exemplary disclosure. Additionally, other polymers may be used which are biocompatible, can provide hydrogels and are cross-linkable according to the invention. Many synthetic polymers and proteins, optionally modified to facilitate gelling and/or cross-linking.

PAG was prepared for the exemplary hydrogels according to the method of Haug et al., reported in *Acta. Chem. Scand.*, 20: p. 183–190 (1966), which disclosure is incorporated herein in its entirety. According to this method, the alginate material underwent acid hydrolysis to break down the β-glycosidic linkages between mannuronate and guluronate residues, thereby providing a lowered molecular weight PG which is essentially lacking mannuronic acid units. The PG was then isolated at pH 2.85, and determined by size-exclusion chromatography (SEC) to have a molecular weight (Mw) of 7,000 (Mw/Mn=1.60). SEC was performed on a triple detector system including a laser refractometer (LR40, VISCOTEK), a differential viscometer, and RALLS (T60, VISCOTEK), 0.1 M NaNO$_3$ buffer solution (pH 6.3) was used as a mobile phase with a flow rate of 0.7 ml/min. Two TSK-gel columns (G4000PW$_{XL}$ and G3000PW$_{XL}$) were used for separation.

Further purification of the PG precipitate was carried out by dissolving the PG in double distilled water at neutral pH, to which activated carbon was added. The resultant solution was thoroughly stirred, the activated carbon removed by filtration, and PG precipitated by ethanol and lyophilized.

The isolated PG was oxidized at room temperature with 0.25 M sodium periodate (ALDRICH, Milwaukee, Wis.) to prepare PAG. The ratio between guluronate units and periodate was 1:1. After 19 hours of oxidation, an equimolar amount of ethylene glycol was added to arrest the reaction. The resultant solution was filtered and precipitated by ethanol. The collected precipitate was redissolved in double distilled water and dialyzed (MWCO 1000, SPECTRA/POR) for 3 days, following which the solution was concentrated under reduced pressure and lyophilized. The Mw of the PAG was 5,700 (Mw/Mn=1.64) as determined by SEC, and the degree of oxidation was determined to be 66.5% (defined by the number of oxidized guluronate residues per 100 guluronate units) by measuring the number of aldehyde groups in the PAG. This measurement was taken by adding an excess amount of t-butyl carbazate to PAG solution, and measuring the amount of unreacted t-butyl carbazates through the addition of trinitrobenzene sulfonic acid (TNBS) solution (the colored complex of t-butyl carbazates and TNBS was quantified spectrophotometrically at 334 nm).

Preferably, the molecular weight of the hydrogel polymer material so prepared is at or below the renal threshold for clearance by the host, whether human or other, which reduction in molecular weight can be effected by the oxidation reaction described above with reference to the exemplary alginate polymer.

Those of ordinary skill will understand that the method of preparing the hydrogel polymer for the exemplary hydrogel of this disclosure is not intended to be limiting of the present invention, according to which a variety of polymers, including the preferred oxidized polysaccharides, prepared according to the above or other known methods, may be substituted in the hydrogel system.

The PAG so obtained was cross-linked with varying amounts of AAD (ALDRICH, Milwaukee, Wis.), a bi-functional cross-linker. Cross-linking of the PAG and AAD occurs in the absence of a catalyst or additive, as aldehyde groups are known to be much more reactive towards hydrazide groups as compared to carboxyl groups. While AAD is a preferred cross-linker for the exemplary hydrogel, other preferred cross-linking agents include compounds with at least two functional groups capable of reversibly cross-linking the hydrogel polymer. Preferred functional groups are hydrazide groups, and any multi-hydrazide cross-linkers will be suited to this invention. However, it will be understood that the functional groups may vary according to such factors as the hydrogel polymer employed. The cross-linker may comprise amine groups, for example. In a hydrogel system comprising aldehyde and multi-hydrazide functional groups, it will also be understood that the functional groups of the polymer and cross-linker may be reversed from the exemplary hydrogel; that is, the cross-linker may comprise aldehyde functional groups, while the hydrogel polymer comprises the hydrazide groups.

In formation of the exemplary hydrogels, a 20 wt % solution of PAG was admixed with AAD in concentrations of from 50 mM to 250 mM. All such solutions were prepared in Dulbecco's Modified Eagle's Medium (DMEM) (LIFE TECHNOLOGIES, Grand Island, N.Y.) having an adjusted pH of 7.4 prior to mixing. The final concentration of PAG in the hydrogel was fixed at 6 wt %. The hydrogel solution was plated in tissue culture plates and incubated at room temperature for 4 hours to permit hydrogel formation. Coupling of aldehyde and hydrazide groups was confirmed by FP-ir spectra on an AVATAR 360 spectrophotometer (NICOLET, Wisconsin) using the KBr pellet method (resolution 2 $cm^{-1}$ with 32 scan repetition). Upon coupling, a characteristic symmetric vibrational band of the aldehyde group at 1735 $cm^{-1}$ disappears, and a hydrazone band at 1658 $cm^{-1}$ appears.

The chemical structure of PAG covalently cross-linked with AAD, the exemplary hydrogel, is shown as follows:

Experimental Results

Forty-eight hydrogels were prepared per the above method, using AAD as the cross-linker in concentrations varying from 50 mN to 250 mM. All of the hydrogels so formed were immersed in DMEM (pH 7.4) at 37° C. for 24 hours to permit complete hydration prior to evaluation for degradation and mechanical characteristics.

At a concentration of 50 mM AAD the resultant hydrogels were very weak and disintegrated prior to complete hydration.

At a concentration of 250 mM AAD no hydrogels formed, presumably owing to the large excess of cross-linking molecules in relation to PAG. It is theorized that an over abundance of dangling, single-end cross-linking molecules prevent any significant cross-linking.

The PAG hydrogels formed with AAD concentrations varying from 100 mM to 200 mM were tested for extent of effective cross-linking, degradation behavior and mechanical properties, the latter two over time. As previously stated, the cross-linked PAG hydrogel is characterized by an absorption band at 1658 $cm^{-1}$ corresponding to the hydrazone bond between the PAG aldehyde group and the AAD hydrazide group. As a result of hydrogel degradation, the hydrazone linkages are hydrolyzed in the presence of aqueous media. This loss of hydrazone linkages can be measured by FT-ir spectra using the KBr pellet method (resolution 2 $cm^{-1}$ with 32 scan repetition), as absorption by the characteristic hydrazone band becomes progressively weaker over time. FIG. 1 is illustrative for PAG and a PAG hydrogel cross-linked with AAD at a concentration of 150 mM; where the band at (a) is PAG, the band at (b) is the PAG hydrogel, the band at (c) is the PAG hydrogel after 5 days degradation, the band at (d) is the PAG hydrogel after 15 days degradation, and the band at (e) is the PAG hydrogel after 29 days degradation. The arrow in FIG. 1 indicates the hydrazone band at 1658 $cm^{31\ 1}$.

A trinitrobenzene sulfonic acid solution (TNBS) was utilized to determine the extent of effective cross-linking (double-end), pendent groups during the cross-linking reaction (dangling single-end), and unreacted cross-linking molecules. Briefly, hydrogels were synthesized, lyophilized, and followed by treatment with TNBS solution (5.76 mM) for 1

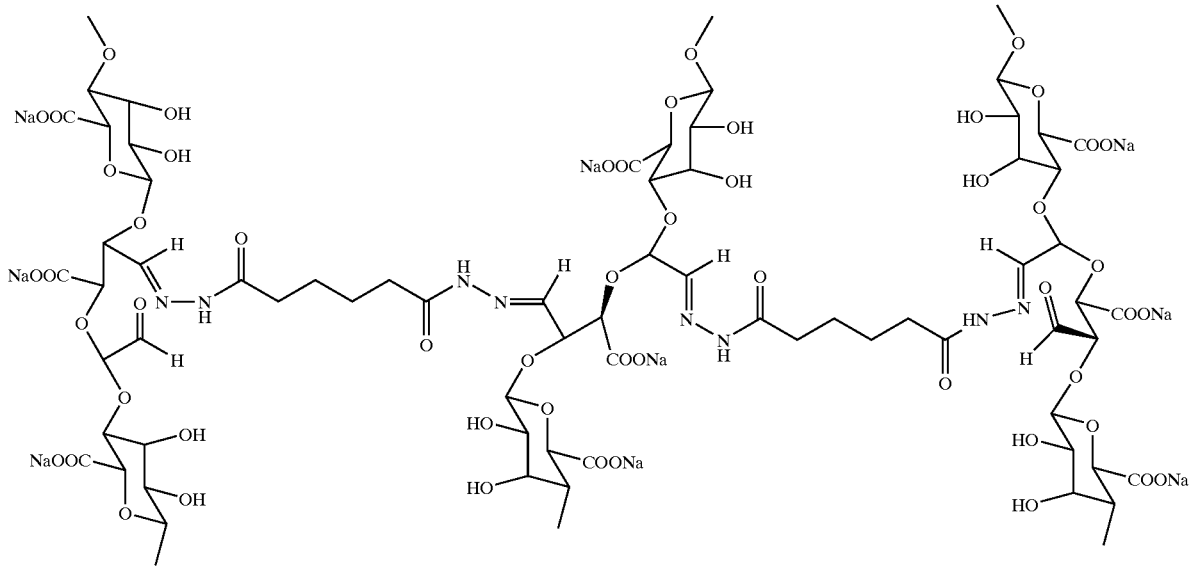

hr. The mixture was filtered through a 0.22-μm filter and the filtrate was used for this assay. The unreacted AAD in the hydrogel reacts with two equivalents of TNBS and forms a soluble complex. The complex solution was diluted with 0.5 N HCl and its amount was spectrophotometrically determined at 334 nm. Dangling single-end AAD molecules form a complex with one equivalent of TNBS, and in this case the complex remains bound to the hydrogel and will not be measured in the previous solution. Therefore, an excess amount of AAD was subsequently added to the filtrate to react with remaining TNBS. The amount of complex bound to the hydrogel was calculated by subtracting the amount of soluble complex from the total amount of TNBS initially added to the hydrogel. Subtracting the amount of unreacted and single-end AAD molecules from the total amount of AAD used yields the cross-linking efficiency, as shown in Table 1.

$cm^3/mol$), and $v_2$ is the volume fraction of polymer in the hydrogel when it reaches the equilibrium swelling state. See Bell et al., *Biomaterials*, 17: p. 1203 (1996). $X_I$ is assumed to be 0.35 on the basis of previous modeling of similar interactions. See Figuly et al., *Macromolecules*, 30: p. 6174 (1997), $f$ is assumed to be 4. Higher cross-linking density corresponds to stiffer mechanical properties and a lower degree of swelling in hydrogels.

Table 1 provides characteristics data for exemplary PAG hydrogels including AAD in concentrations from 100 mM to 200 mM. Data include cross-linking efficiency, shear moduli (G), swelling ratio ($Q_m$), degree of swelling (Q), and cross-linking density ($V_e$), all as defined above.

TABLE 1

Characteristics of PAG Hydrogels Cross-linked with Different Concentration of AAD

| AAD | cross-linking efficiency (%) | | | | | | $(v_e)_0$ |
|---|---|---|---|---|---|---|---|
| (mM) | unreacted | single-end | double-end | $G_0$ (kPa) | $Q_m$ | Q | ($\times 10^5$ mol/cm$^3$) |
| 100 | 4.1 | 11.9 | 84.0 | 6.1 ± 0.5 | 13.2 ± 0.2 | 12.6 ± 0.2 | 16.0 ± 0.5 |
| 150 | 4.2 | 19.9 | 75.9 | 7.5 ± 0.8 | 12.8 ± 0.4 | 12.2 ± 0.3 | 17.1 ± 0.9 |
| 200 | 5.9 | 35.0 | 59.1 | 1.4 ± 0.2 | 16.0 ± 0.6 | 15.3 ± 0.6 | 11.1 ± 0.8 |

The mechanical strength of the exemplary hydrogels formed according to the present invention was measured by compression testing with an MTS BIONIX 100 mechanical tester (MTS SYSTEMS, France) to obtain an elastic modulus in compression. The deformation rate was 0.5 mm/min and the indentor had a diameter of 3.15 mm. The shear modulus (G) of the hydrogels was determined by the slope of $\sigma v. -(\lambda-\lambda^2)$, where $\sigma$ is the stress and $\lambda$ is the ratio of deformed length: undeformed length of the hydrogel (assuming an affine network model) as disclosed in Treloar, *Physics of Rubber Elasticity* (Clarendon Press: Oxford, 1975), and Stainsby, *Food Chemistry*, 6: p. 3(1980), both of which disclosures are incorporated herein by reference in their entireties.

The hydrogels so prepared were also measured for swelling. As indicated, all of the hydrogels were immersed in DMEM (pH 7.4) for 24 hours at 37° C., following which excess water was removed and the hydrogels weighed. The degree of swelling (Q) in the hydrogels was defined as the reciprocal of the volume fraction of polymer in the hydrogel ($v_2$) using the following equation:

$$Q = v_2^{-1} = [(1/\rho_p)[(Q_m/\rho_s)+(1/\rho_p)]^{-1}]^{-1}$$

Where $\rho_p$ is the polymer density (0.87555 g/cm$^3$ for sodium alginate), $\rho_s$ is the density of water (0.9971 g/cm$^3$ at 25° C.), and $Q_m$ is the swelling ratio, defined as the mass ratio of absorbed water and the dried hydrogel. See DeRossie et al., *Polymer Gels Fundamentals and Biomedical Applications* (Plenum Press, New York 1991).

Cross-linking density of the exemplary hydrogels prepared according to the above method was calculated by the Flory-Rehner equation:

$$V_e = [\ln(1-v_2) + v_2 + X_I v_2^2][V_1(v_2^{1/3} - 2v_2/f)]^{-1}$$

Where $X_I$ is the interaction parameter, $f$ is the cross-linking functionality, $v_1$ is the molar volume of water (18.062 cm$^3$/mol), and $v_2$ is the volume fraction of polymer in the hydrogel when it reaches the equilibrium swelling state.

As shown, the PAG hydrogels with initially higher cross-linking density ($V_e$) (i.e., hydrogels cross-linked with 100 mM and 150 mM AAD) but lower single-end dangling cross-linkers exhibited initially stiffer mechanical properties and lower degrees of swelling, as evidenced by the shear moduli (G) and swelling ($Q_m$, Q) data. The PAG hydrogels with a higher percentage of single-end dangling cross-linkers exhibited less stiff initial mechanical properties.

Degradation Characteristics

Figure 2:
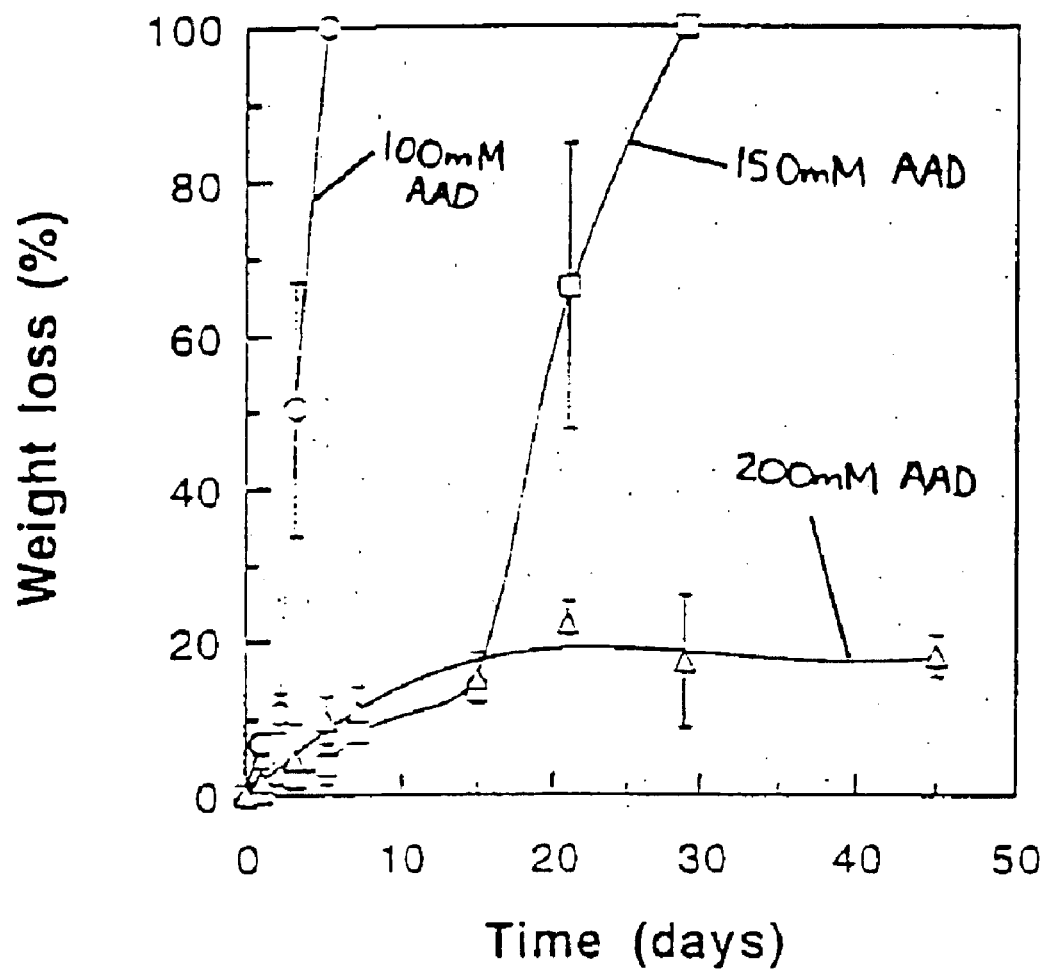
FIG. 2 is a plot of weight loss (%) over time for exemplary PAG gels prepared with AAD cross-linker in concentrations of 100 mM (○), 150 mM (□), and 200 mM (Δ).

Since the reaction between aldehydes and hydrazides is very fast, it is expected that the resulting hydrazone bonds will be liable to hydrolysis, and therefor that any hydrogels so formed will degrade in aqueous media by bulk erosion. Surprisingly and unexpectedly, however, the exemplary hydrogels of the present invention formed with an AAD concentration of 200 mM, and thus characterized by cross-linking densities of less than 16.0×10$^5$ mol/cm$^3$, but a higher portion of dangling cross-linkers exhibited slower degradation than comparative hydrogels having 100 mM or 150 mM AAD concentrations, despite having these lower cross-linking densities as determined by the Flory-Rehner equation. (TABLE 1.) These surprising and unexpected results, obtained according to the methods outlined above, are evidenced by the following:

Particularly, hydrogel dry weight loss was measured as a function of degradation time. (FIG. 2) PAG hydrogels having an AAD concentration of 100 mM (○) exhibited 100% weight loss (complete degradation) inside of 10 days, while those with an AAD concentration of 150 mM (□) degraded completely within 30 days. However, the hydrogels with 200 mM AAD (Δ) exhibited minimal weight loss (<20%) even after 6 weeks incubation in DMEM (pH 7.4) at 37° C.

Figure 3:
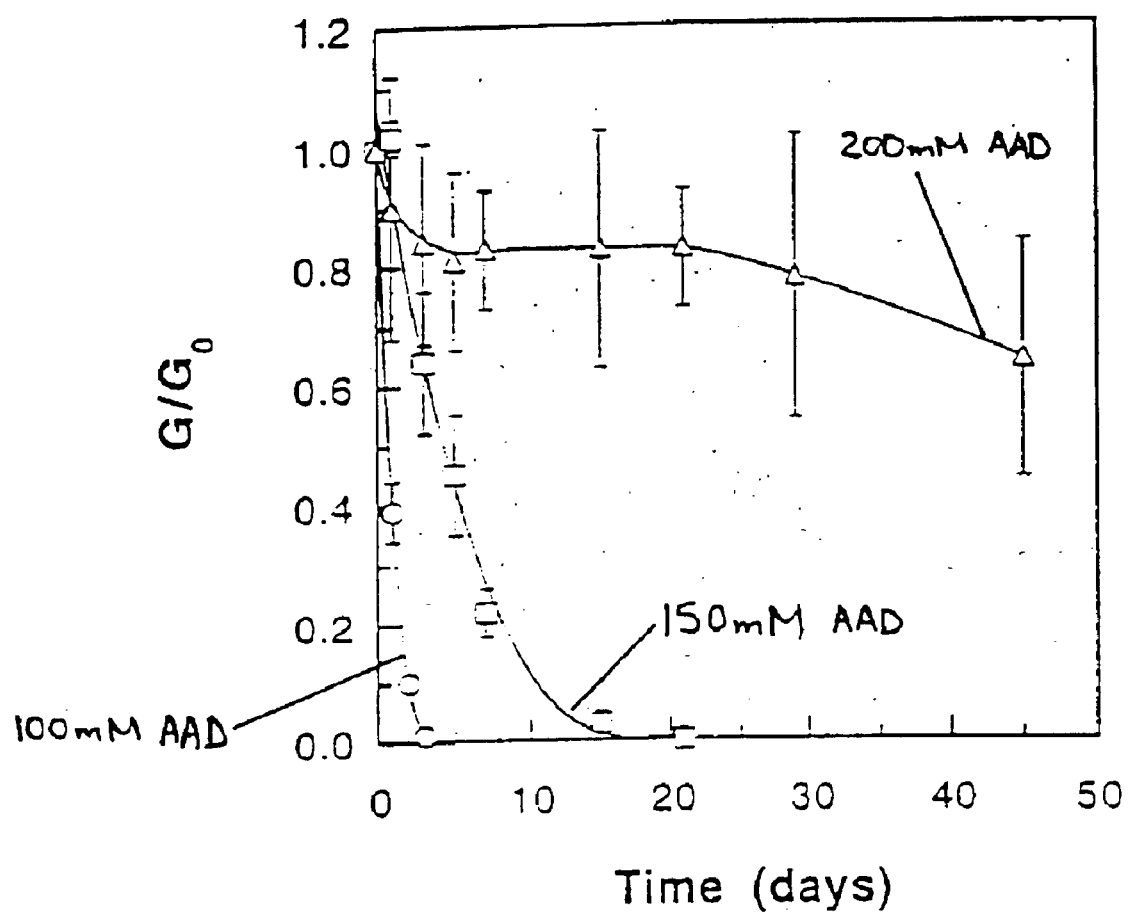
FIG. 3 is a plot of shear modulus change ($G/G_0$) over time for exemplary PAG hydrogels prepared with AAD cross-linker in concentrations of 100 mM (○), 150 mM (□), and 200 mM (Δ).

FIG. 3 shows the change over time in shear modulus (G/G$_0$) of comparative PAG hydrogel examples cross-linked with 100 mM (○) and 150 mM (□) AAD, and PAG hydrogels prepared with 200 mM (Δ) concentration of AAD. All of the hydrogels were incubated in DMEM (pH 7.4) at 37° C. As shown, mechanical strength was rapidly lost for the 100 mM and 150 mM AAD hydrogels, while the 200 mM AAD hydrogel of the present invention, despite the low cross-linking density (TABLE 1), displayed significantly less reduction in mechanical strength over the duration of the evaluation period.

Figure 4:
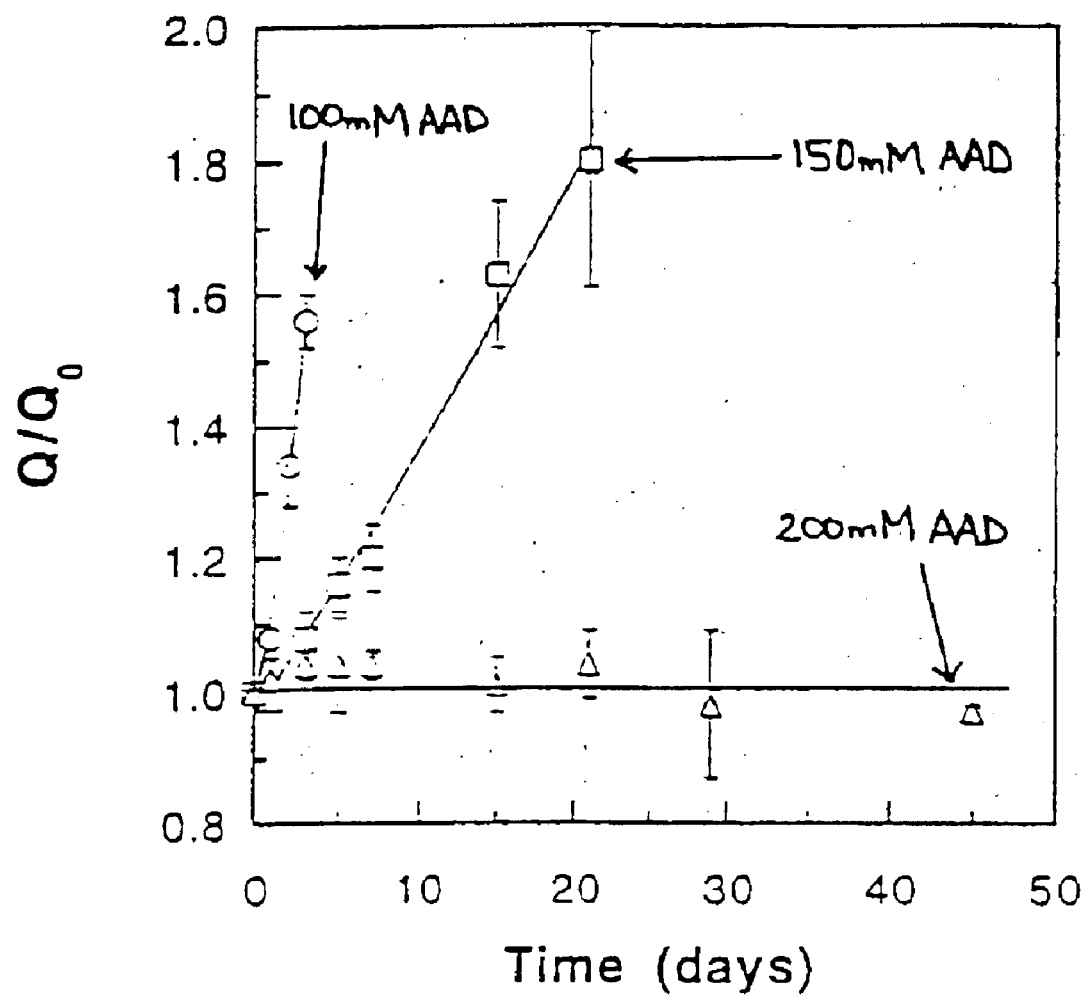
FIG. 4 is a plot of change in degree of swelling ($Q/Q_0$) over time for exemplary PAG hydrogels prepared with AAD cross-linker in concentrations of 100 mM (○), 150 mM (□), and 200 mM (Δ).

FIG. 4 shows the change in degree of swelling ($Q/Q_0$) over time for PAG hydrogels cross-linked with AAD in concentrations of 100 mM (○), 150 mM (□), and 200 mM (Δ). All of the hydrogels were incubated in DMEM (pH 7.4) at 37° C. These data reflect the relative stability of low cross-linking density hydrogels prepared according to the present invention. Particularly, the hydrogels of the comparative examples, cross-linked with 100 mM and 150 mM AAD, exhibited increased swelling over the course of degradation, while hydrogels cross-linked with 200 mM AAD showed no significant change.

Figure 5:
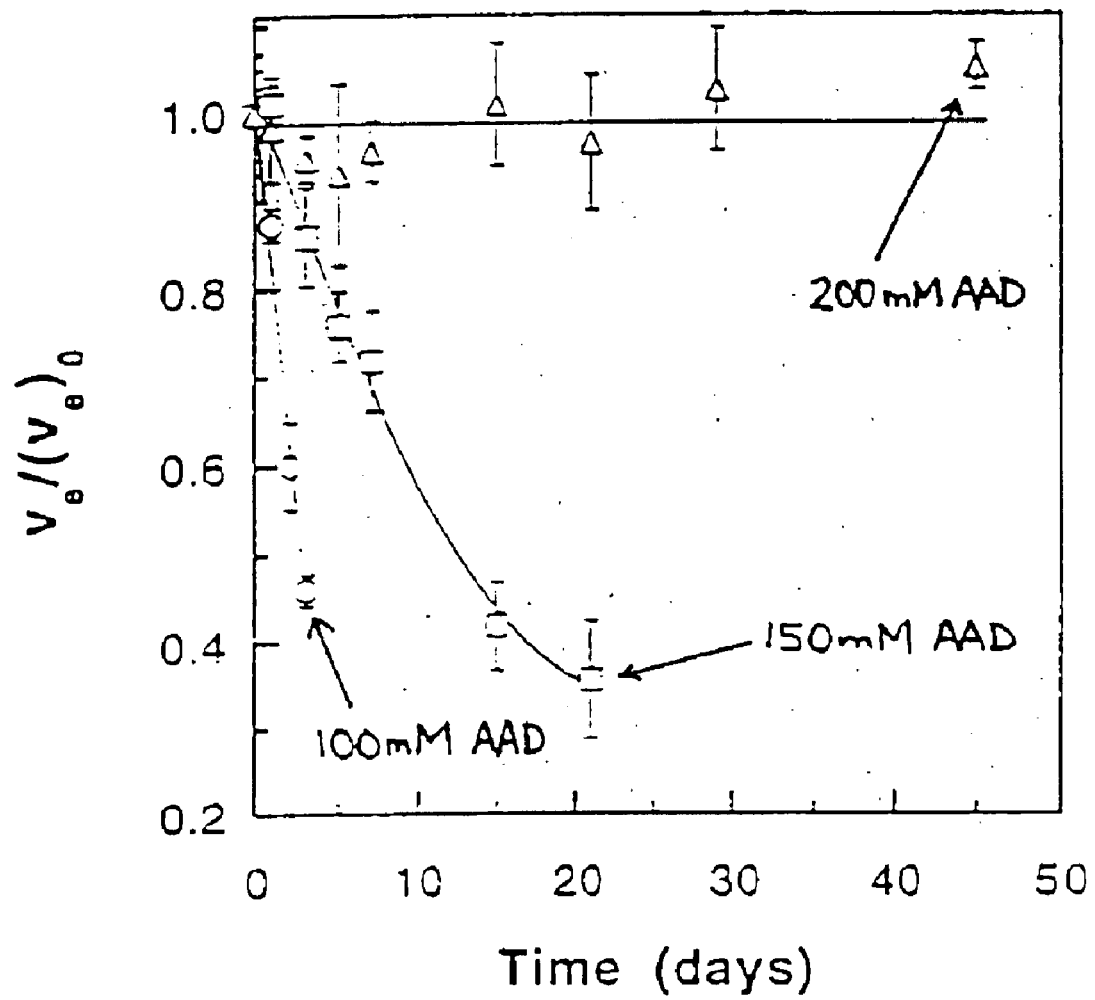
FIG. 5 is a plot of change in cross-linking density ($V_e/(V_e)_0$) over time for exemplary PAG hydrogels prepared with AAD cross-linker in concentrations of 100 mM (○), 150 mM (□), and 200 mM (Δ).
Figure 6:
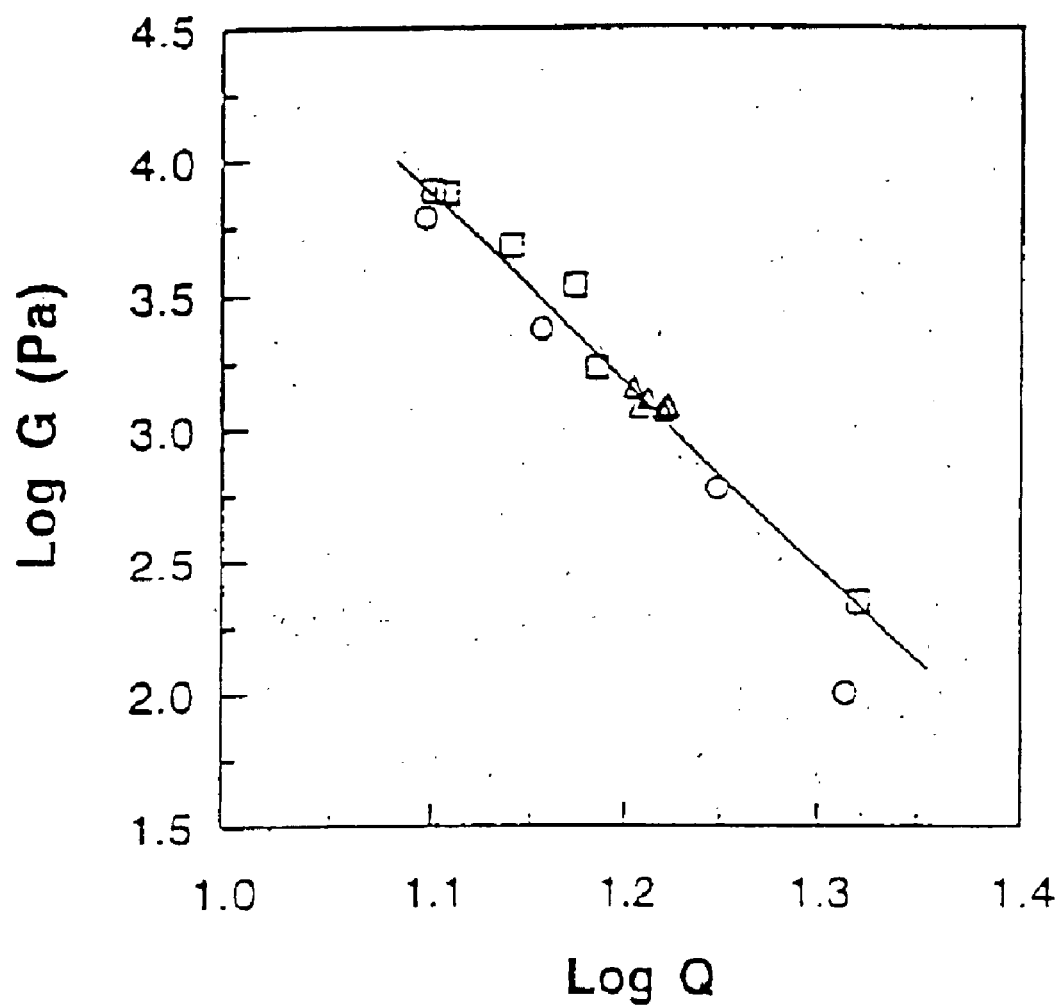
FIG. 6 is a plot of shear modulus (G) versus degree of swelling (Q) for exemplary AG.

FIG. 5 shows the change in cross-linking density ($V_e/(V_e)_0$) over time for PAG hydrogels cross-linked with AAD in concentrations of 100 mM (○), 150 mM (□), and 200 mM (Δ). As already indicated, cross-linking density ($V_e$) was calculated using the Flory-Rehner equation. In the case of FIG. 5, these data are supported by the linear relationship (FIG. 6) between the shear modulus (G) and degree of swelling (Q) after degradation for hydrogels having AAD in each of the three concentrations, 100 mM (○), 150 mM (□), and 200 mM (Δ), which relationship suggests Gaussian elasticity justifying use of the Flory-Rehner equation.

The improved degradation characteristics of the hydrogels of the present invention result from the relatively high concentration of dangling, single-end cross-linker molecules in the multi-hydrazide cross-linking agent, which molecules permit reversible-cross-linking with the hydrogel polymer following hydrolysis of the initial cross-linking bond to retain stability over time. While it has previously been considered that retarded degradation was effected by increasing cross-linking density, which approach yielded hydrogels with undesirable mechanical properties, the present invention surprisingly and unexpectedly provides a hydrogel and method of making the same wherein the mechanical and degradative properties of the hydrogel may be decoupled by the utilization of a cross-linking agent capable of reversibly cross-linking the polymer, resulting in a relatively mechanically "soft" hydrogel but with retarded degradation characteristics.

What we claim is:

1. A hydrogel composition comprising a hydrogel polymer, which polymer is a natural or synthetic alginate, optionally hydrolyzed and/or oxidized, and which polymer is prepared using an excess amount of cross-linker having two or more functional groups capable of cross-linking the polymer such that the polymer has cross-links to other hydrogel polymer molecules and also has dangling cross-linkers with at least one functional group bound to a hydrogel polymer and at least one unbound functional group capable of reversibly cross-linking the polymer, wherein the amount of dangling cross-linkers, based on the total amount of cross-linkers bound to the polymer by at least one functional group, is from 20% to 90%.

2. The hydrogel composition of claim 1, wherein the amount of dangling cross-linkers is from 20% to 70%.

3. The hydrogel composition of claim 1, wherein the amount of dangling cross-linkers is from 30% to 50%.

4. The hydrogel composition of claim 1, wherein the hydrogel polymer is an alginate which has been hydrolyzed to poly(guluronate) and oxidized to a poly(aldehyde guluronate).

5. The hydrogel composition of claim 1, wherein the hydrogel polymer has a weight average molecular weight of 1,000 to 50,000 dalton.

6. The hydrogel composition of claim 1, wherein the hydrogel polymer has a weight average molecular weight of 1,000 to 30,000 dalton.

7. The hydrogel composition of claim 1, wherein the hydrogel polymer has a weight average molecular weight of 1,000 to 10,000 dalton.

8. The hydrogel composition of claim 1 wherein the hydrogel polymer before cross-linking has a molecular weight such that it is at or below the renal threshold of humans.

9. The hydrogel composition of claim 1, wherein the cross-linker has at least two hydrazide functional groups.

10. The hydrogel composition of claim 1, wherein the cross-linker is adipic acid dihydrazide.

11. The hydrogel composition of claim 1, wherein the hydrogel has an initial shear modulus of 0.005 to 200 kPa.

12. The hydrogel composition of claim 1, wherein the hydrogel has an initial shear modulus of 0.05 to 100 kPa.

13. The hydrogel composition of claim 1, wherein the hydrogel polymer is a synthetic alginate.

14. A method for tissue engineering, cell transplantation or drug delivery which comprises administering to a subject in need thereof a composition comprising a hydrogel composition of claim 1.

* * * * *